United States Patent
Chen et al.

(10) Patent No.: US 11,839,428 B1
(45) Date of Patent: Dec. 12, 2023

(54) METHOD FOR ANALYZING DISTRIBUTION OF RETINAL LESIONS IN MOUSE MODEL

(71) Applicant: JOINT SHANTOU INTERNATIONAL EYE CENTER OF SHANTOU UNIVERSITY AND THE CHINESE UNIVERSITY OF HONG KONG, Shantou (CN)

(72) Inventors: Haoyu Chen, Shantou (CN); Xiaoting Mai, Shantou (CN); Shaofen Huang, Shantou (CN); Meiqin Zhang, Shantou (CN)

(73) Assignee: JOINT SHANTOU INTERNATIONAL EYE CENTER OF SHANTOU UNIVERSITY AND THE CHINESE UNIVERSITY OF HONG KONG, Shantou (CN)

( * ) Notice: Subject to any disclaimer, the term of this patent is extended or adjusted under 35 U.S.C. 154(b) by 0 days.

(21) Appl. No.: 18/309,855

(22) Filed: May 1, 2023

(30) Foreign Application Priority Data

Aug. 15, 2022 (CN) .......................... 202210971164.3

(51) Int. Cl.
*A61B 3/00* (2006.01)
*A61B 3/12* (2006.01)
*A61B 3/10* (2006.01)

(52) U.S. Cl.
CPC ............ *A61B 3/0025* (2013.01); *A61B 3/102* (2013.01); *A61B 3/12* (2013.01)

(58) Field of Classification Search
CPC .......... A61B 3/0025; A61B 3/102; A61B 3/12
See application file for complete search history.

(56) References Cited

U.S. PATENT DOCUMENTS

2021/0312596 A1   10/2021   Hagiwara
2021/0330393 A1   10/2021   Govari

FOREIGN PATENT DOCUMENTS

| CN | 109919179 A | 6/2019 |
| CN | 110163844 A | 8/2019 |
| CN | 110490860 A | 11/2019 |
| CN | 113222038 A | 8/2021 |
| CN | 114334124 A | 4/2022 |

(Continued)

OTHER PUBLICATIONS

Benjamin et al. "Spatiotemporal Patterns of Tumor Occurrence in Children with Intraocular Retinoblastoma" (Year: 2015).*

(Continued)

*Primary Examiner* — Vu Le
*Assistant Examiner* — Winta Gebreslassie
(74) *Attorney, Agent, or Firm* — Kaplan Breyer Schwarz, LLP; Stuart H. Mayer

(57) ABSTRACT

Disclosed is a method for analyzing a distribution of retinal lesions in a mouse model, including: scanning a mouse posterior polar fundus based on optical coherence tomography (OCT), and acquiring lesion images of the mouse posterior polar fundus; acquiring lesion distribution coordinates based on the lesion images of the mouse posterior polar fundus; constructing a coordinate map of a lesion distribution rule based on the lesion distribution coordinates; and acquiring lesion distribution in quadrants based on the coordinate map of the lesion distribution rule, and calculating and counting a number of lesions in each quadrant.

6 Claims, 9 Drawing Sheets

(56) References Cited

FOREIGN PATENT DOCUMENTS

| CN | 114581375 A | 6/2022 |
| CN | 114782337 A | 7/2022 |
| JP | 2017142491 A | 8/2017 |

OTHER PUBLICATIONS

Gesine et al. "Spectral Domain Optical Coherence Tomography in Mouse Models of Retinal Degeneration" (Year: 2009).*

Cazañas-Gordón, et al. "Ensemble Learning Approach to Retinal Thickness Assessment in Optical Coherence Tomography" IEEE access, vol. 9, 2021.

Mai et al. "Application of Optical Coherance Tomography to a mouse model of retinopathy" Jove Journal of Visualized Experiments, Jan. 2022.

Yingzi, "Application of Improved Goolenet based on weak supervision in DR detection" Journal of Computer Applications, 2019, 39(8) 2484-2488.

\* cited by examiner

METHOD FOR ANALYZING DISTRIBUTION OF RETINAL LESIONS IN MOUSE MODEL

CROSS-REFERENCE TO RELATED APPLICATIONS

This application claims priority to Chinese Patent Application No. 202210971164.3, filed on Aug. 15, 2022, the contents of which are hereby incorporated by reference.

TECHNICAL FIELD

The application belongs to the technical field of biomedicine, and in particular to a method for analyzing a distribution of retinal lesions in a mouse model.

BACKGROUND

A mouse model is often used in studying retinal diseases. Optical coherence tomography (OCT) is often used to study retina phenotypic characteristics in the mouse model. According to a paper description (ISSN: 1940-087X) about an application of OCT in the mouse model of retinopathy published in a video magazine JoVE, OCT is an imaging technology that may provide high-resolution and cross-sectional imaging in vivo for tissues, especially suitable for a non-invasive examination of retina. In addition, OCT may be used to quantify some important biomarkers, such as a retinal thickness and a retinal nerve fiber layer thickness, and is widely used in ophthalmology diagnosis and treatment as an important tool for diagnosis, follow-up and treatment of patients with retinal diseases. OCT may also provide clues for understanding pathogenesis of the retinal diseases. OCT may be used not only in clinical diagnosis and treatment, but also in an animal research. In the animal research, although pathology is a gold standard of morphological characteristics, OCT has advantages of non-invasive imaging in vivo and longitudinal follow-up, which is beneficial to observe an occurrence and a development of retinopathy. Moreover, in a study of animal models of retinopathy, manifestations of OCT are closely related to histopathology. In a biomedical research, mice are the most used animals. However, small sizes of mice eyeballs bring technical challenges to OCT imaging. The paper 1940-087X has introduced in detail how to use OCT to examine retinas of mice, including how to find retinal lesions, how to analyze morphological characteristics of the retinal lesions and how to measure retinal thicknesses.

Patent CN201310357899.8 discloses a method for a multi-parameter measurement of a mouse retina in vivo. In this method, an OCT instrument is used to scan fundus images of a mouse retina, and a high-definition single-line scanning mode is used to obtain a panretinal sectional image of a mouse and measure a thickness of each layer on the mouse retina. An average thickness and an average volume of 9 sub-regions of the mouse retina are measured by a retinal volume model, and morphology of the mouse retina is reconstructed in three dimensions. Continuous thickness data of retinal nerve fiber layers are obtained by an optic disc scanning mode. However, this method is mainly aimed at an analysis of retinal thickness/thicknesses and overall morphology, and there is no targeted analysis method of the retinal lesions.

According to a patent CN201910188403.6, a convolutional neural network algorithm in a deep learning model is used to construct a classifier to realize a classification of retinopathy, and an image segmentation algorithm is used for a lesion extraction and retina layering. However, this method needs certain research conditions, especially an artificial intelligence experimental platform. In a practical work of clinical diagnosis and treatment, not all medical units have such conditions. In an experimental study of animal models, it is even more difficult to have such research conditions. For animal experiments, a cost of this method is too high and an operability is poor.

Because the mouse retina has no macula, the mouse may not fix its vision when taking pictures at the fundus, and a direction of retinal rotation in the fundus is not fixed. In a study of mouse retinopathy, it is difficult to locate the lesion accurately. OCT presents a cross-section of the retina, so which layer of the retina is invaded by a certain lesion may be judged through an OCT examination of the mouse model of retinopathy. However, cross-sectional information alone may not reflect overall location characteristics of the lesions. At present, there is also a lack of a simple and intuitive analysis method that may combine the cross-sectional information and quadrant distribution information of the lesions. In a study of mouse retinopathy model, there is no analysis method to reflect a distribution of the retinal lesions by OCT data and fundus photos.

SUMMARY

An objective of the application is to provide a method for analyzing a distribution of retinal lesions in a mouse model, so as to solve problems existing in the prior art.

In order to achieve the above objective, the application provides the method for analyzing the distribution of the retinal lesions in the mouse model, including:

scanning a mouse posterior polar retina based on optical coherence tomography (OCT), and acquiring lesion images of the mouse posterior polar retina;

acquiring lesion distribution coordinates based on the lesion images of the mouse posterior polar retina, constructing a coordinate map of a lesion distribution rule based on the lesion distribution coordinates;

acquiring a retinal layering distribution based on the coordinate map of the lesion distribution rule, and calculating and counting lesion distribution quadrants; and counting a number of lesions based on the retinal layering distribution.

Optionally, a process of acquiring the retina of the lesion images of the mouse posterior polar fundus based on OCT scanning includes:

acquiring a scanning line and a marker point based on a scanning position of OCT;

starting scanning with the scanning line passing through an optic papilla in a horizontal direction or a vertical direction, moving the scanning line with a width of one marker point, and carrying out intensive scanning in an order of top-bottom-nasal side-temporal side to observe whether there is a lesion; and moving the marker point to the lesion and taking a picture when the lesion is found.

Optionally, if the scanned lesion is large, or the same lesion is scanned continuously, a picture of a most obvious lesion feature on one OCT image of the mouse posterior polar retina is taken.

Optionally, the lesion distribution coordinates include retinal layers with lesions and lesion center coordinates, and a process of acquiring the lesion distribution coordinates based on the lesion images of mouse posterior polar fundus includes:

acquiring and marking the retinal layers with the lesions based on the lesion images of the mouse posterior polar fundus;

measuring a linear distance between each lesion center and an optic papilla center in the lesion images of the mouse posterior polar fundus, wherein the optic papilla center is a center of a mouse posterior pole;

measuring an angle between a connecting line from each lesion center to the optic papilla center and a bottom edge in the lesion images of the mouse posterior polar fundus, wherein the bottom edge is a straightest, thickest and unbranched blood vessel in an upper retina; and constructing a coordinate system, and acquiring the lesion center coordinates based on the linear distance between each lesion center and the optic papilla center and the angle between the connecting line from each lesion center to the optic papilla center and the bottom edge.

Optionally, a process of acquiring the lesion center coordinates based on the linear distance between each lesion center and the optic papilla center and the angle between the connecting line from each lesion center to the optic papilla center and the bottom edge includes:

taking the optic papilla center as a coordinate zero point, substituting the linear distance between each lesion center and the optic papilla center and the angle between the connecting line between each lesion center and the optic papilla center and the bottom edge into a sine formula and a cosine formula, and respectively calculating values of the connecting line from each lesion center to the optic papilla center projected on an x axis and a y axis of the coordinate system, and acquiring the lesion center coordinates.

Optionally, a process of constructing the coordinate map of the lesion distribution rule based on the lesion distribution coordinates includes:

setting the retinal layers as categorical variables, and classifying and marking retinal layering, and representing by numbers; and generating the coordinate map of the lesion distribution rule based on an x-axis coordinate, a y-axis coordinate and a retina layering number of each lesion.

Optionally, a process of acquiring the retinal layering distribution based on the coordinate map of the lesion distribution rule, and calculating and counting the lesion distribution quadrants includes:

calculating and recording the quadrants with lesion coordinates based on an IF function tool; recording as 0 when there is no lesion in the quadrants; recording as 1 when one lesion is located in a first quadrant, recording as 2 when one lesion is located in a second quadrant, recording as 3 when one lesion is located in a third quadrant, recording as 4 when one lesion is located in a fourth quadrant, and recording as 5 when one lesion is located in a coordinate axis; and classifying recorded results according to an eye type, a mouse type and a location, and generating distribution quadrant histograms by a statistical analysis with a t test.

Optionally, a process of counting the number of lesions based on the retinal layering distribution includes:

counting the number of lesions respectively based on the t test according to the retinal layering involved in the lesions in OCT, and generating histograms of the number of lesions.

The application has technical effects as follows.

The method mentioned in the application only needs to measure two parameters: one is a distance between each lesion and the optic papilla center on each cSLO fundus photo, and an other is an angle formed by the connecting line between each lesion center and the optic papilla center and an upper retinal vein. According to these two parameters, the lesion coordinates are obtained by a theorem that when two lines are parallel, internal dislocation angles are equal and a trigonometric function law, and coordinate marking of lesion center points is realized. Combining the lesion coordinates with the retinal layers involved in the lesions, one coordinate map is deduced, intuitively presenting a distribution rule of retinal lesions. This method integrates cross-sectional layering information (OCT) and quadrant position distribution information (fundus photography) of the retinal lesions in the mouse model, and comprehensively reflects positions of mouse retinal lesions. The method provided by the application provides a suitable image analysis method for an animal model research of retinopathy.

An angle measurement method mentioned in the application solves a problem that a direction of the retina is not fixed due to rotation of a mouse eyeball when taking pictures. Because a mouse retina has no macula, the mouse may not fix its vision during the fundus photography, and a direction of retinal rotation in the fundus photo is not fixed. Because of the above problems, it is difficult to accurately locate the mouse retinal lesions. There is a blood vessel in the upper retina of each mouse. This blood vessel has characteristics of thick, straight and unbranched, and is different from other blood vessels and easy to distinguish. This blood vessel is the upper retinal vein. In the application, this blood vessel is used for positioning and is taken as the bottom edge for an angle measurement and the y axis in the coordinate map, so that a difficulty of the angle measurement is reduced and a reference for lesion positioning is provided.

In addition, an IF function formula is designed in the application according to a relationship between x values, y values and 0 in the coordinates. The method mentioned in the application realizes rapid classification and marking of the lesion positions only according to the lesion coordinates calculated by the two parameters, so as to carry out the statistical analysis on the number of lesions in each quadrant.

BRIEF DESCRIPTION OF THE DRAWINGS

Accompanying drawings constituting a part of this application are used to provide a further understanding of this application. Illustrative embodiments and descriptions of this application are used to explain this application, and do not constitute an improper limitation of this application.

DETAILED DESCRIPTION OF THE EMBODIMENTS

It should be noted that embodiments in this application and features in the embodiments may be combined with each other without conflict. The present application is described in detail with reference to attached drawings and embodiments.

It should be noted that steps shown in a flowchart of the attached drawings may be executed in a computer system such as a set of computer-executable instructions. Moreover, although a logical order is shown in the flowchart, in some cases, the steps shown or described may be executed in a different order from here.

Embodiment 1

Figure 9:
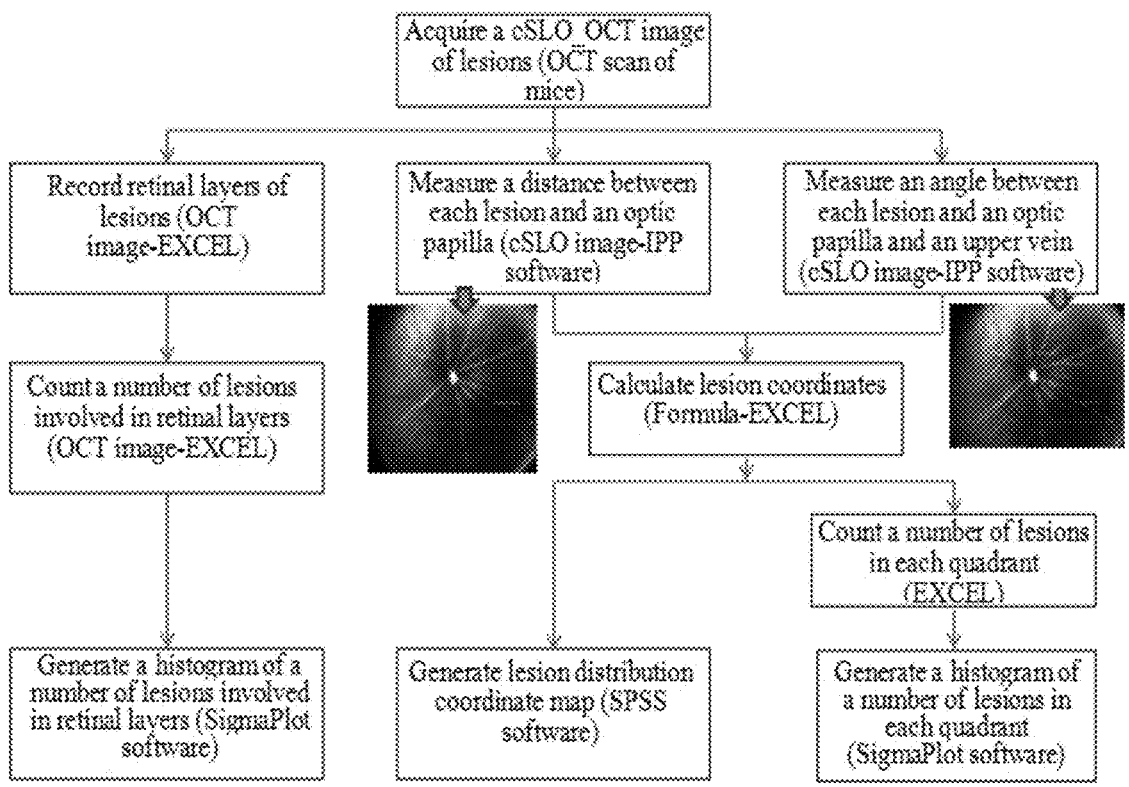
FIG. 9 is a flowchart of a method for analyzing a distribution of retinal lesions in a mouse model according to an embodiment of the application.

As shown in FIG. 9, this embodiment provides a method for analyzing a distribution of retinal lesions in a mouse model.

Optical coherence tomography (OCT) image acquisition requirements: images analyzed by this method are generated by an OCT scanning mode of a Roland fundus imaging system of small animals; posterior polar fundus images of mice with an optic papilla as a center are required to obtain to distinguish eyes; there is a marker line marking an OCT scanning position on one real-time corresponding fundus photo, and there is a dot mark on the marker line marking a lesion position on each OCT image; a scanning line passing through an optic papilla in a horizontal direction (or vertical direction) is used for initial scanning, and the scanning line is moved with a width of one marker point to carry out intensive scanning on each quadrant to observe whether there is a lesion; if the lesion is found, a picture is taken after the marker point is moved to the lesion; and if the lesion is large and the same lesion is scanned continuously, a picture taken at a most obvious lesion feature on the OCT image is selected for an analysis; and only one picture scanned in one direction needed to be selected for the analysis for the same eyeball during a picture selection for the analysis (scanning results of a horizontal scanning line and a vertical scanning line are repeated, so the results may be used as a reference or supplement, but only one is needed for the analysis). A paper 1940-087X is referred to for an image acquisition method.

Data acquisition method:

S1, recording retinal layers where the lesions are located in the OCT image: recording the retinal layers across which the lesions cross according to the retinal layers of OCT (a retinal nerve fiber layer RNFL, a ganglion cell layer GCL, an inner plexiform layer IPL, an inner nuclear layer INL, an outer plexiform layer OPL, an outer nuclear layer ONL, an outer membrane ELM, a photoreceptor inner segment IS, a photoreceptor outer segment OS, and a RPE-Bruch membrane complex), and recording results in an EXCEL table and marking different retinal layers with numbers.

S2, measuring a linear distance between a lesion center and an optic papilla center in the fundus photo: opening Image-Pro Plus, importing a cSLO-OCT image, clicking on a Measurements window, selecting a linear measurement button, measuring a scale length (Pixels) in the cSLO image, and measuring a distance (Pixels) between a lesion marker point and the optic papilla center with a linear measurement tool, and recording data in the EXCEL table; and converting length data according to the scale length, where a length unit is µm;

S3, taking a straightest, thickest and unbranched blood vessel (an upper retinal vein) of an upper retina as a bottom edge on the fundus photo, and measuring an angle between a connecting line between the lesion center and the optic papilla center and the bottom edge: opening the Image-Pro Plus, importing the cSLO-OCT image, clicking on the Measurements window, and selecting an angle measurement button; finding out the straightest, thickest and unbranched blood vessel in the upper retina, following an orientation of this blood vessel, first clicking a mouse at a far end of the orientation (without releasing) and dragging the mouse to the optic papilla center, and then releasing the mouse at the optic papilla center to draw the bottom edge; clicking the mouse at the optic papilla center (without releasing) and then dragging the mouse to the lesion marker point, and releasing the mouse at the lesion marker point to draw a hypotenuse; reading an angle value on the image or in the Measurements window, and recording angle data in the EXCEL table.

Figure 1:
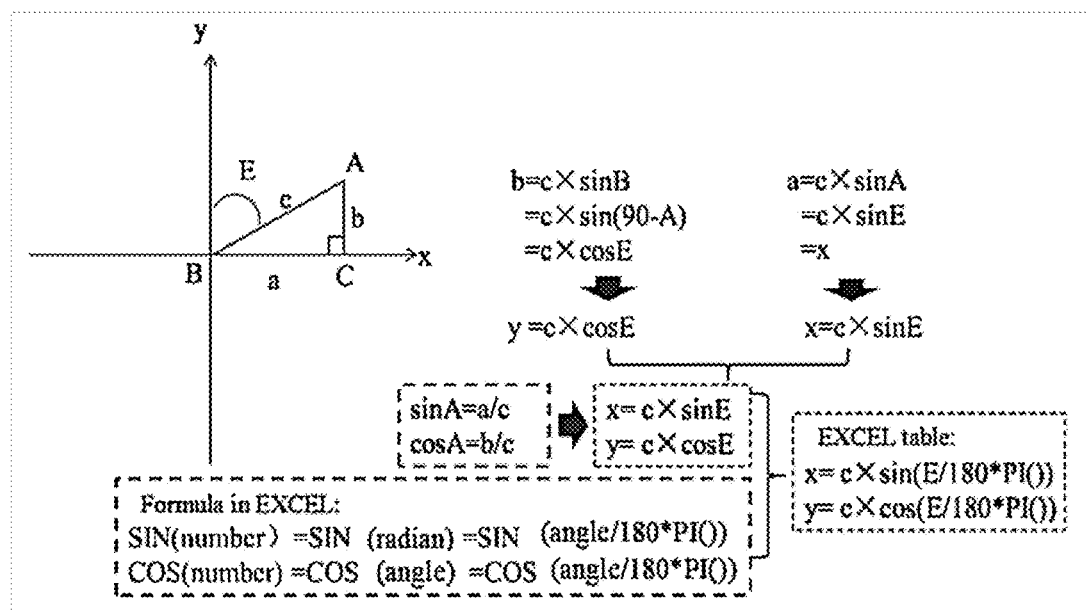
FIG. 1 is a train of thought for calculating coordinates (x,y) of retinal lesions found in optical coherence tomography (OCT) in an embodiment of the application.
Figure 2:
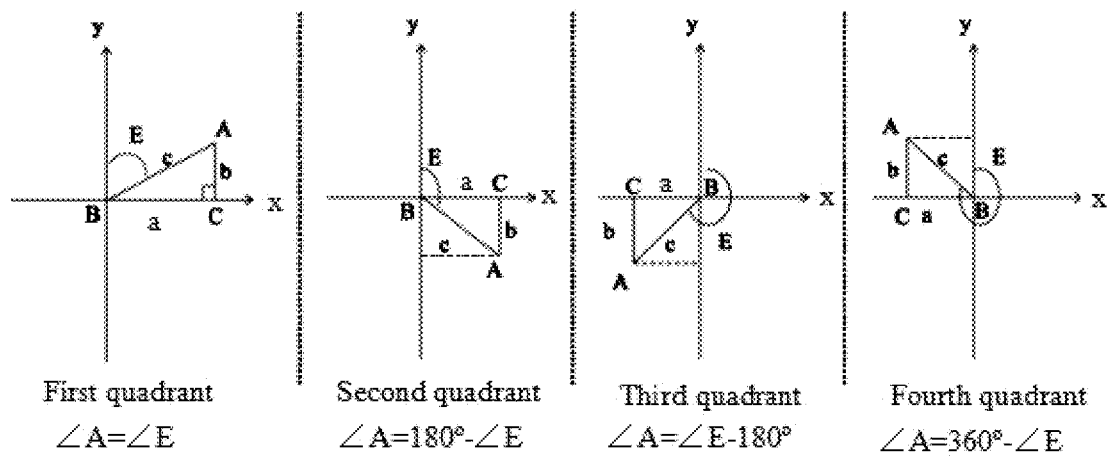
FIG. 2 is a relationship diagram of ∠E and ∠A in a right triangle formed by a lesion-optic papilla line and an x-axis coordinate in different quadrants in an embodiment of the application.

S4, drawing coordinates: taking a horizontal direction as an x axis and a vertical direction as a y axis, where the y axis represents the orientation of the upper retinal vein (i.e., the straightest, thickest and unbranched upper blood vessel, the bottom edge of an angle to be measured); taking the connecting line from the lesion center (point A) to the optic papilla center (point B) as the hypotenuse (recorded as AB); taking the optic papilla center (point B) as a coordinate zero point, where an angle between the y-axis and AB represents the angle between the connecting line between the lesion center and the optic papilla center and the bottom edge and is denoted as ∠E; according to a length value of the hypotenuse AB (a hypotenuse length is denoted as c, and the unit is µm), calculating values of AB projected on the x-axis and the y-axis respectively by using a sine formula (sinE=SIN(E/180*PI()), x=c×sinE) and a cosine formula (cosE=COS(E/180*PI()), y=c×cosE)to obtain the coordinates (x, y) of the lesion center (point A) in the EXCEL. FIG. 1 and FIG. 2 show the above calculation methods and principles.

Results presentation method:

1. Distribution rule-coordinate box plot: IBM SPSS Statistics21.0 (SPSS Inc, Chicago, Ill.) is opened and three variables (retinal layer, x-axis coordinate value and y-axis coordinate value) are established, and the retinal layer is set as a categorical variable to classify and mark retinal layering, and the retinal layering is represented by numbers. An x-axis coordinate, a y-axis coordinate and a retina layering number of each lesion is input in a data input interface. Graph (G) is clicked, Chart Builder is selected, Basic Element is selected in a pop-up window, Axis Selection is double-clicked to select 2D Coordinate, and the variable of x-axis coordinate value in a Variable (V) column is dragged to Is it x-axis in an editing area, and the variable of y-axis coordinate value is dragged to Is it y-axis in the editing area. Notes or names of the x-axis and the y-axis may be added in Axis Label of an Element Properties window. Point Map in Select Element in a Basic Element column is selected and dragged to the editing area. A Grouping/Stack Variable (G) item under Group/Point ID is checked, and then a Set Color box is appeared in the editing area. The categorical variable of retina layer in the Variable (V) column is dragged into the Set Color box. A title, a subtitle, a color, etc. may be modified in a Title/Footnote window and the Element Properties window. OK is clicked and a box plot is generated in an output window. The box plot is double-clicked to open Chart Editor, an icon of Add Reference Line to X Axis is clicked, a position of Reference Line in a Properties window is modified to 0.0, and properties of Reference Line in Line are modified. An icon of Add Reference Line to Y Axis is clicked, the position of Reference Line in the Properties window is modified to 0.0, and the properties of Reference Line in Line are modified. Total Fitting Line is selected in the Element column of Icon Editor, Loess (O) in the pop-up Properties window is selected to modify Percentage of Points to Fit (P), and properties of Fitting Line in the Line column are modified. Apply is clicked and Chart Editor is closed, and a picture may be exported from the output window.

A coordinate map generated by the above methods may visually display the distribution of different color circles marking the retinal layers in different retinal quadrants. Because a nasal direction and a temporal direction of each fundus image of the left and right eyes are opposite, the images of the left and right eyes need to be made separately. In order to highlight characteristics of target mice, data collection and image generation of control mice should be carried out simultaneously. As may be clearly observed from the coordinate box plots in this case, the lesions in the right eye (FIG. 3) and left eye (FIG. 4) of the target mouse were significantly more than those in the right eye (FIG. 5) and left eye (FIG. 6) of the control mouse, mainly located in the lower quadrant, and marked colors tended to an outer retina.

2. Quadrant distribution statistics:

In the EXCEL table, an IF function tool is used to calculate the quadrants where lesion coordinates are located. A function formula is:

IF(AND(x="None",y="None"),0,IF(AND(x>0,y>0),1,IF(AND(x>0,y<0),2,IF(AN D(x<0,y<0),3,IF(AND(x<0,y>0),4,IF(OR(x=0,y=0),5))))))

Figure 7:
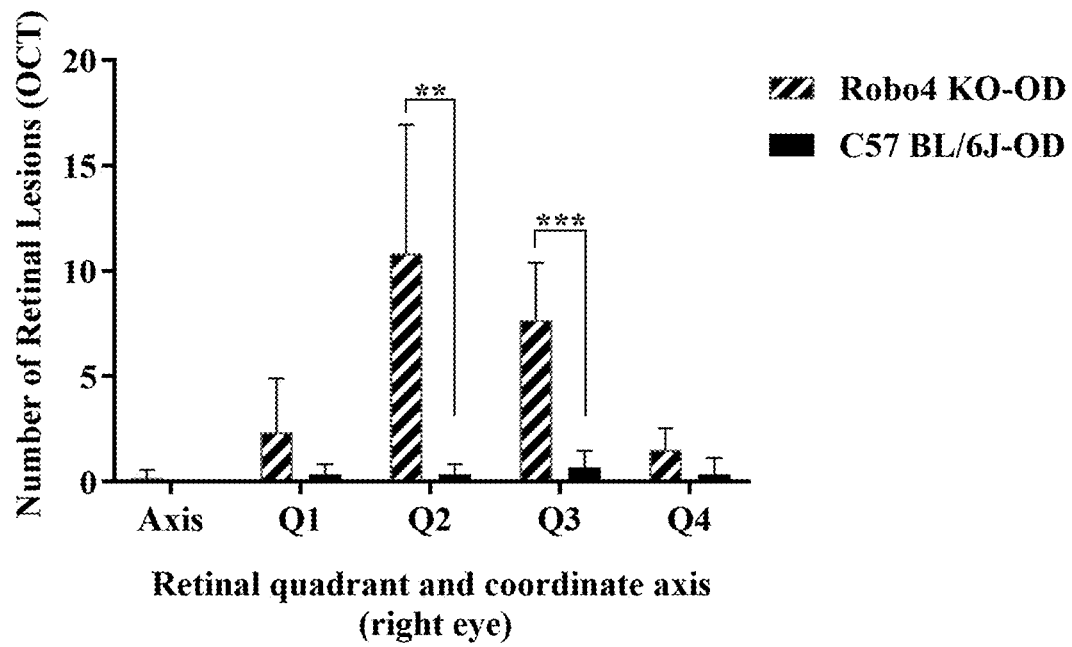
FIG. 7 shows histograms of comparison results of number of lesions in each quadrant between an experimental group and a control group in an embodiment of the application.
Figure 7:
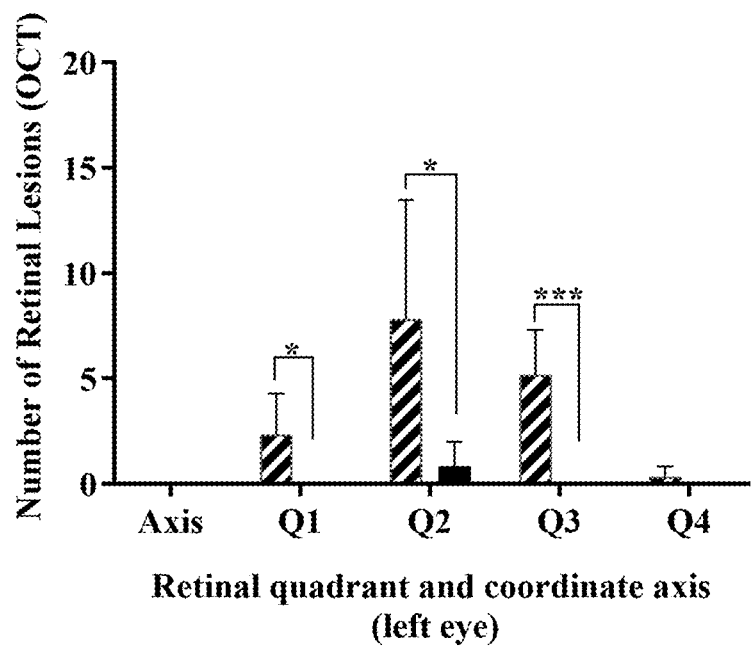

If there is no lesion in the quadrants, the lesion is recorded as 0; and the lesion in a first quadrant is recorded as 1, in a second quadrant as 2, in a third quadrant as 3, in a fourth quadrant as 4 and in the coordinate axis as 5. The results were sorted according to an eye type, a mouse type and a position, and were statistically analyzed by a t test. Histograms were generated by a drawing software SigmaPlot 12.5 (Systat Software, Inc., San Jose, Calif.), as shown in FIG. 7. Because the nasal direction and the temporal direction of each fundus image of the left eye and the right eye are opposite, the data of the left eye and the right eye need to be counted separately.

Figure 8:
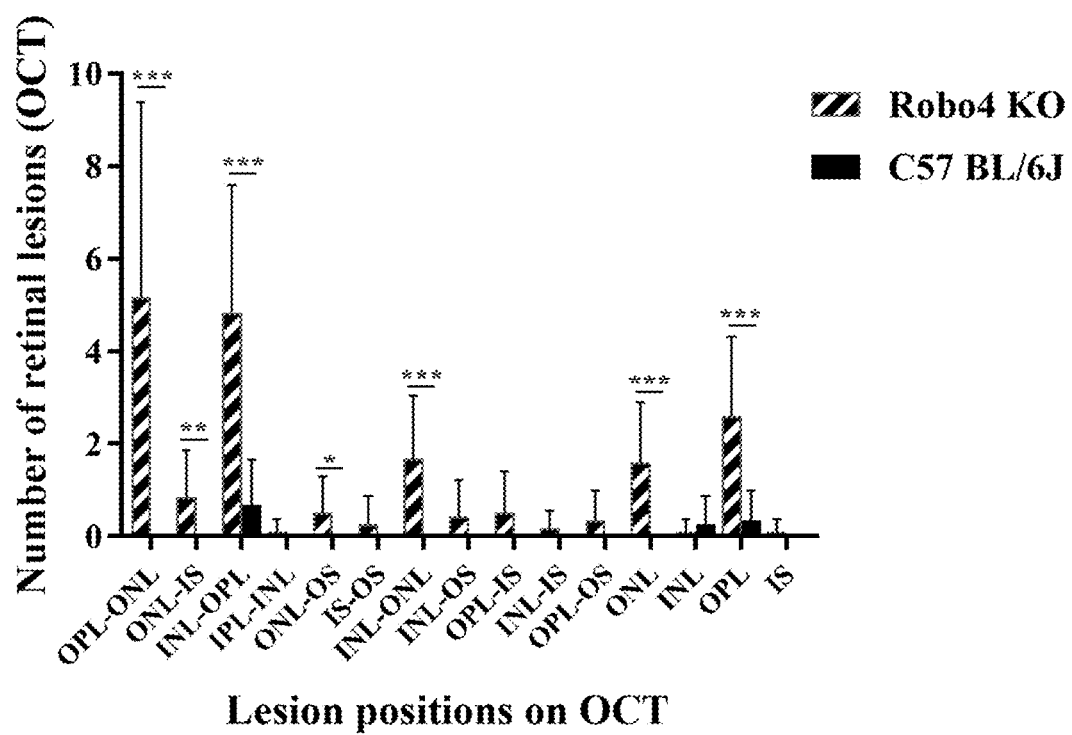
FIG. 8 is a histogram of comparison results of number of lesions in involved retinal layers in OCT images of an experimental group and a control group in an embodiment of the application.

3. Retinal layering distribution statistics:

numbers of the lesions are counted separately according to the retinal layering involved in the lesions in OCT (There is no need to distinguish between eyes, only an experimental group and a control group), and the statistics is made by the t test, and the histograms are generated by the drawing software SigmaPlot 12.5 (Systat Software, Inc., San Jose, Calif.), as shown in FIG. 8.

Embodiment 2

As shown in FIGS. 1-8, this embodiment provides an application example of a method for analyzing a distribution of retinal lesions in a mouse model.

The OCT scanning is performed on Robo4 gene knockout mice (Robo4 KO) by using the Roland fundus imaging system of small animals. The control group is C57 BL/6J, and there are 6 mice in each group with an age of 1.5 months. OCT images with high reflective lesions are obtained.

A yellow dot in one cSLO image corresponds to a position where a green vertical line passes through the retina in one OCT image, and the green line passes through an edge of the high reflective lesion. A retinal high reflective lesion is located at a position from the inner nuclear layer to the outer plexiform layer (INL-OPL), and is recorded by a user-defined number, such as 3.

Image-Pro Plus is opened, the cSLO-OCT image is imported, the Measurements window is clicked on, the linear measurement button is selected to measure that the scale length of 200 μm in the cSLO image is 96 Pixels, and then the distance between the lesion marker point and the optic papilla center is measured as 453.9273 Pixels, and the distance is recorded in the EXCEL table and converted into the hypotenuse length c: 945.681875 μm.

The straightest, thickest and unbranched blood vessel in the upper retina is looked for on cSLO as a reference (bottom edge). The angle measurement button in the Measurements window is selected, first the mouse is clicked at a far end of a reference blood vessel (without releasing), and the mouse is dragged to the optic papilla center along the general orientation and is released at the optic papilla center to draw the bottom edge. The mouse is clicked at the optic papilla center (without releasing), and then dragged to the lesion marker point, and the mouse is released at the lesion marker point to draw the hypotenuse. A measured value is showed as 125.006° both in the image and the Measurements window and marked as ∠E, and recorded in the EXCEL table.

The coordinates of one lesion (A) is calculated in the EXCEL table. SinE is calculated as 0.819091975 by using the sine formula (sinE=SIN(E/180*PI())), and an abscissa is calculated as 774.6004347 by using a trigonometric function law (x=c×sinE). Similarly, cosE is calculated as −0.573662215 by using the cosine formula (cosE=COS(E/180*PI())), and an ordinate is calculated as −542.5019587 by using a trigonometric function law (y=c×cosE). The coordinates of the lesion are (774.6004347,−542.5019587), and a location is located in the second quadrant and is marked as 2.

All the OCT images with the high reflective lesions are analyzed in a same way, and the coordinates of all the lesions are obtained and recorded.

IBM SPSS Statistics 21.0 (SPSS Inc, Chicago, Ill.) is opened, and the retinal layers, abscissa values and ordinate values of all the lesions are input. Graph (G) is clicked, Chart Builder is selected, Basic Element is selected in the pop-up window, Axis Selection is double-clicked to select 2D Coordinate, and a variable of abscissa value in the Variable (V) column is dragged to Is it x-axis in the editing area, and a variable of ordinate value is dragged to Is it y-axis in the editing area. Axis Label in the Element Properties window is modified. Point Map in Select Element in the Basic Element column is selected and dragged to the editing area. The Grouping/Stack Variable (G) item under Group/Point ID is checked, and then the categorical variable of retina layer in the Variable (V) column is dragged into the Set Color box. The title is added in the Title/Footnote window and the Element Properties window. OK is clicked and the box plot is generated. The box plot is double-clicked to open Chart Editor, the icon of Add Reference Line to X Axis is clicked, the position of Reference Line in the Properties window is modified to 0.0, and properties of Reference Line in Line are modified. The icon of Add Reference Line to Y Axis is clicked, the position of Reference Line in the Properties window is modified to 0.0, and the properties of Reference Line in Line are modified. Total Fitting Line is selected in the Element column of Icon Editor, Loess (O) in the pop-up Properties window is selected, and properties of Fitting Line in the Line column are modified. Apply is clicked and Chart Editor is closed, and the picture is exported.

Figure 3:
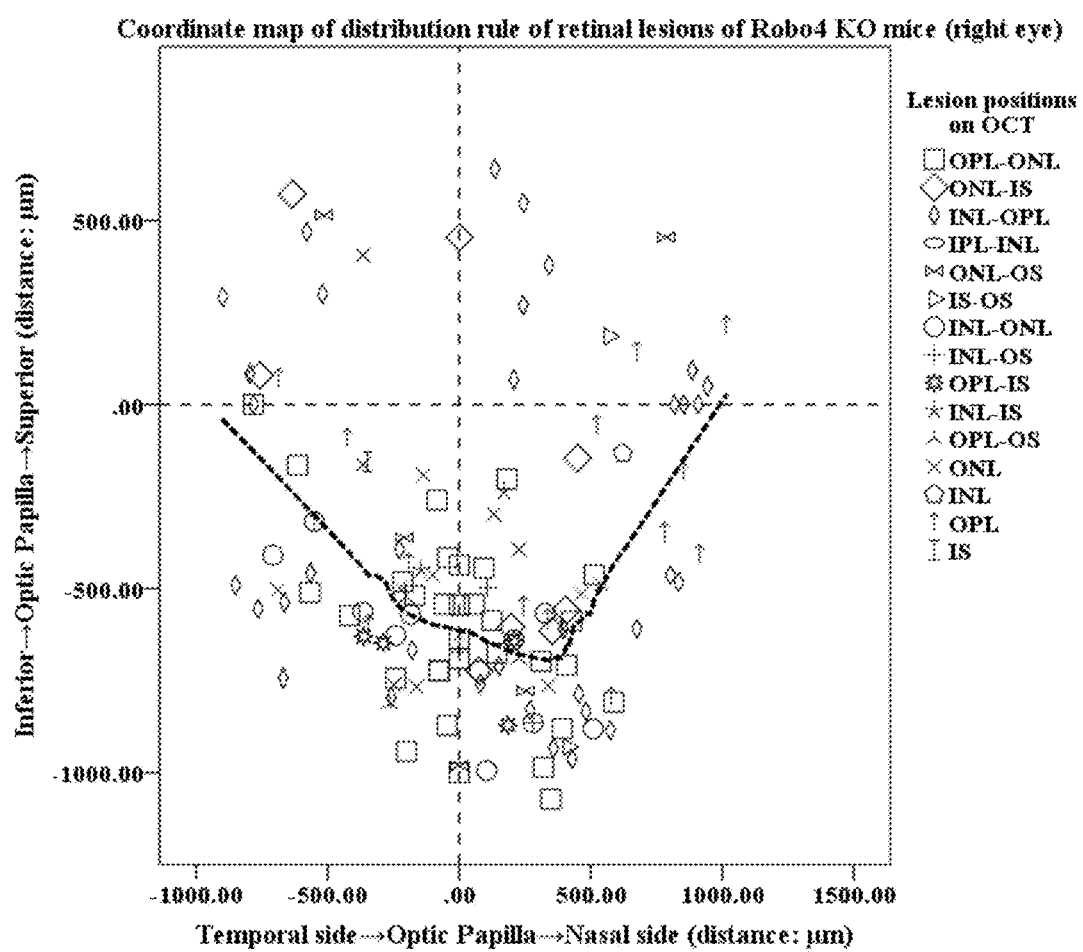
FIG. 3 is a coordinate map of a distribution rule of retinal lesions in right eyes of Robo4 KO mice in an embodiment of the application.

Distribution plots of the retinal lesions in the right eyes and the left eyes of the two groups of mice are compared (FIG. 3). The results show that the number of lesions in Robo4 gene knockout mice increased significantly, and the lesions are mainly concentrated in lower quadrants.

Figure 4:
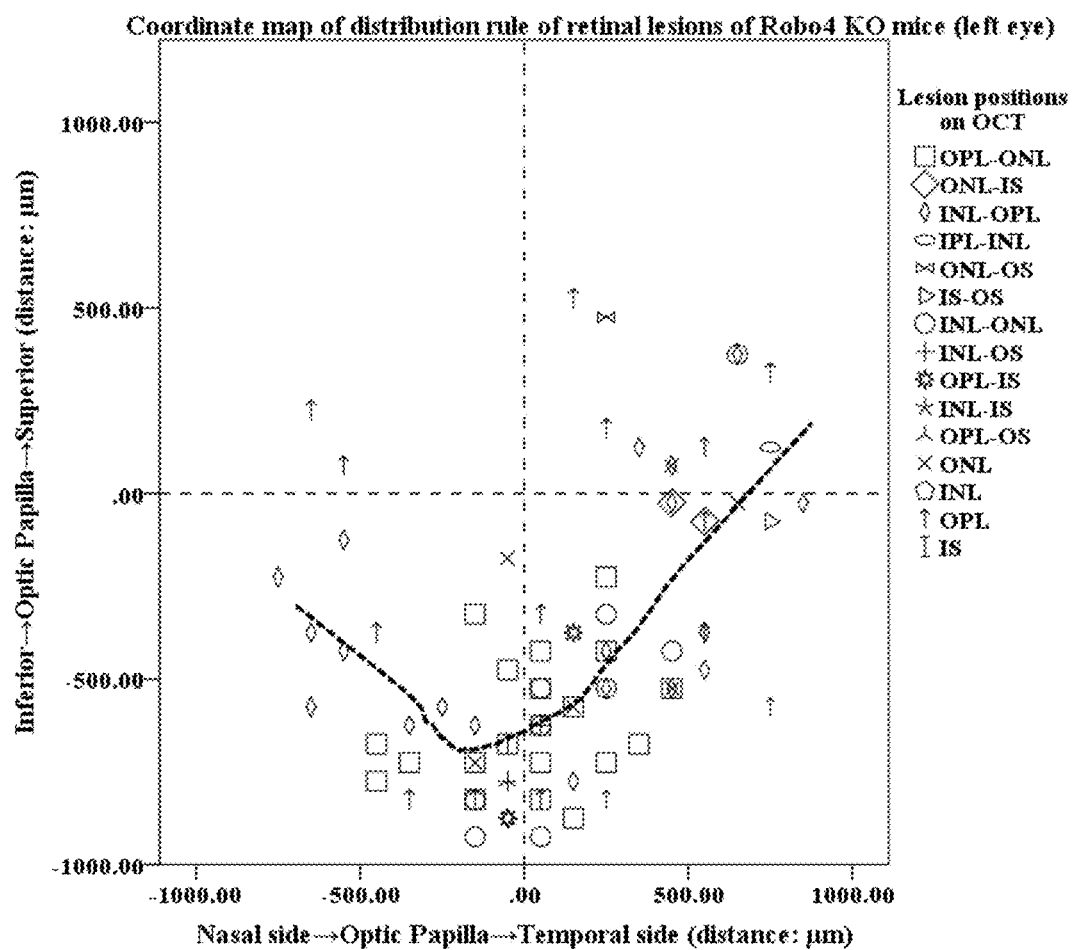
FIG. 4 is a coordinate map of a distribution rule of retinal lesions in left eyes of Robo4 KO mice in an embodiment of the application.

The data in the EXCEL table are sorted according to the eye type, the mouse type and the location, and the number of lesions in each quadrant of each eyeball is counted. The data are input into the drawing software SigmaPlot 12.5 (Systat Software, Inc., San Jose, Calif.). Analyze is clicked, and each row of the data is counted by Multiple t test separately to generate the histograms (FIG. 4). The results show that the retinal lesions of the Robo4 gene knockout mice increase significantly in the right eyes in the second and third quadrants and in the left eyes in the first, second and third quadrants.

Figure 5:
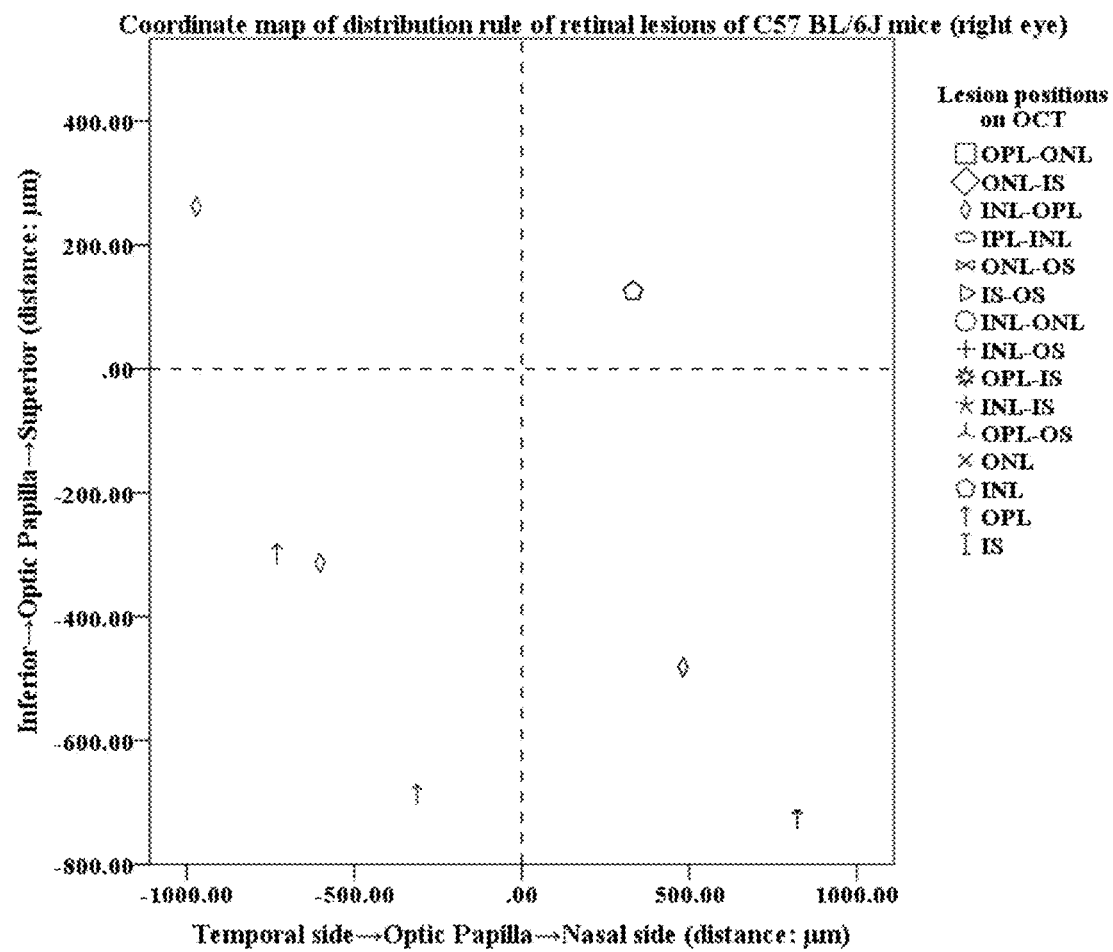
FIG. 5 is a coordinate map of a distribution rule of retinal lesions in right eyes of C57BL/6J mice in an embodiment of the application.
Figure 6:
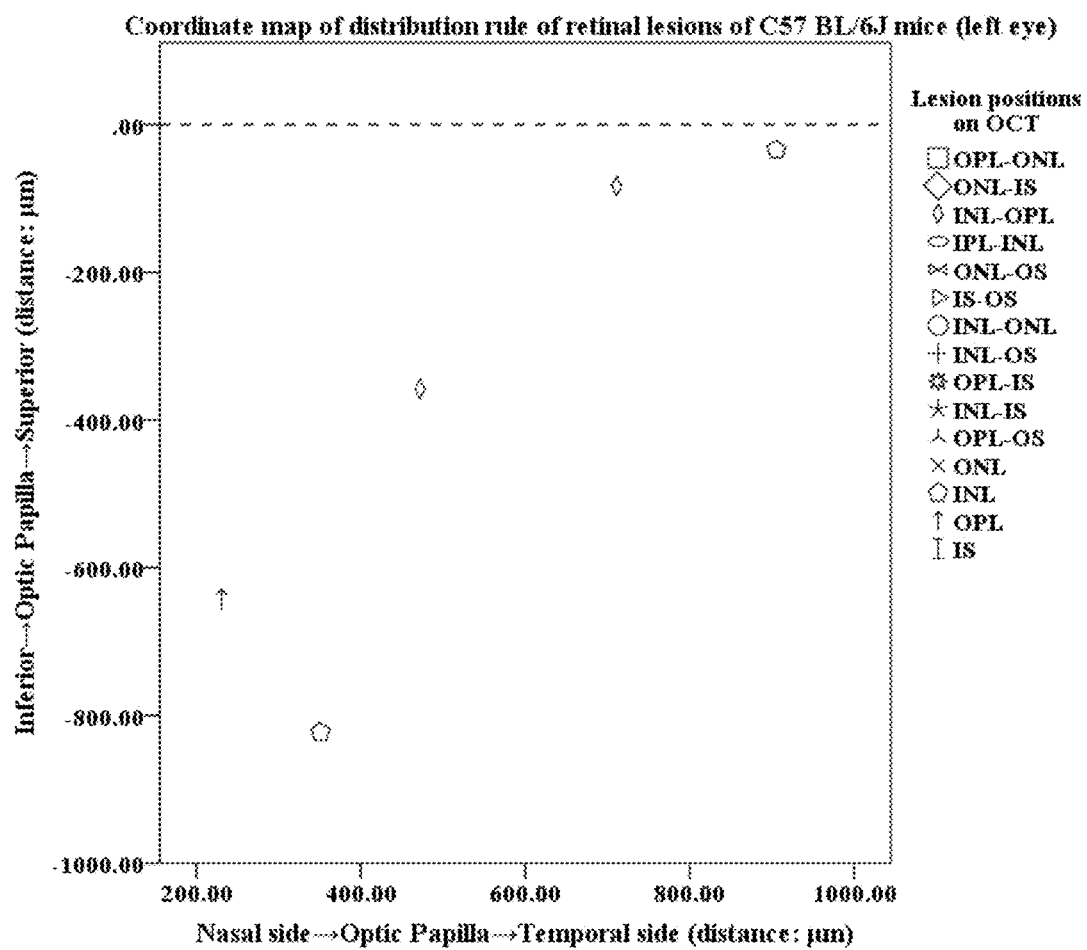
FIG. 6 is a coordinate map of a distribution rule of retinal lesions in left eyes of C57BL/6J mice in an embodiment of the application.

The data in the EXCEL table are sorted according to the mouse type and the retina layers where the lesions are located, and the number of lesions in each eyeball-involved retina layer is counted. The data are entered into the drawing software SigmaPlot 12.5 (Systat Software, Inc., San Jose, Calif.). Analyze is clicked, and each row of the data is counted by Multiple t test to generate a histogram (FIG. 5). The results show that the number of retinal lesions in Robo4 gene knockout mice increases significantly on the layers of OPL-ONL, ONL-IS, ONL-OS, INL-ONL, ONL and OPL. The main retinal layers involved in the lesions are the outer nuclear layer and the outer plexiform layer.

The above is only the preferred embodiments of this application, but a protection scope of this application is not limited to this. Any change or replacement that may be easily thought of by a person skilled in the art within a technical scope disclosed in this application should be covered by this application. Therefore, the protection scope of this application should be based on the protection scope of claims.

What is claimed is:

1. A method for analyzing a distribution of retinal lesions in a mouse model, comprising:
scanning a mouse posterior polar retina based on OCT, and acquiring lesion images of the mouse posterior polar retina;
acquiring lesion distribution coordinates based on the lesion images of the mouse posterior polar retina, wherein the lesion distribution coordinates comprise retinal layers with lesions and lesion center coordinates;
constructing a coordinate map of a lesion distribution rule based on the lesion distribution coordinates;
acquiring a retinal layering distribution based on the coordinate map of the lesion distribution rule, and calculating and counting lesion distribution quadrants; and
counting a number of lesions based on the retinal layering distribution;
a process of acquiring the lesion distribution coordinates based on the lesion images of mouse posterior polar fundus comprises:
acquiring and marking the retinal layers with the lesions based on the lesion images of the mouse posterior polar fundus;
measuring a linear distance between each lesion center and an optic papilla center in the lesion images of the mouse posterior polar fundus, wherein the optic papilla center is a center of a mouse posterior pole;
measuring an angle between a connecting line from each lesion center to the optic papilla center and a bottom edge in the lesion images of the mouse posterior polar fundus, wherein the bottom edge is a straightest, thickest and unbranched blood vessel in an upper retina; and
constructing a coordinate system, and acquiring the lesion center coordinates based on the linear distance between each lesion center and the optic papilla center and the angle between the connecting line from each lesion center to the optic papilla center and the bottom edge;
wherein a process of acquiring the lesion center coordinates based on the linear distance between each lesion center and the optic papilla center and the angle between the connecting line from each lesion center to the optic papilla center and the bottom edge comprises:
taking the optic papilla center as a coordinate zero point, substituting the linear distance between each lesion center and the optic papilla center and the angle between the connecting line between each lesion center and the optic papilla center and the bottom edge into a sine formula and a cosine formula, and respectively calculating values of the connecting line from each lesion center to the optic papilla center projected on an x axis and a y axis of the coordinate system, and acquiring the lesion center coordinates.

2. The method for analyzing the distribution of the retinal lesions in the mouse model according to claim 1, wherein a process of scanning the mouse posterior polar retina based on OCT comprises:
acquiring a scanning line and a marker point based on a scanning position of OCT;
starting scanning with the scanning line passing through an optic papilla in a horizontal direction or a vertical direction, moving the scanning line with a width of one marker point, and carrying out intensive scanning in an order of top-bottom-nasal side-temporal side to observe whether there is a lesion; and
moving the marker point to the lesion and taking a picture when the lesion is found.

3. The method for analyzing the distribution of the retinal lesions in the mouse model according to claim 2, wherein if the scanned lesion is large, or the same lesion is scanned continuously, a picture of a most obvious lesion feature on one OCT image of the mouse posterior polar retina is taken.

4. The method for analyzing the distribution of the retinal lesions in the mouse model according to claim 1, wherein a process of constructing the coordinate map of the lesion distribution rule based on the lesion distribution coordinates comprises:
setting the retinal layers as categorical variables, and classifying and marking retinal layering, and representing by numbers; and generating the coordinate map of the lesion distribution rule based on an x-axis coordinate, a y-axis coordinate and a retina layering number of each lesion.

5. The method for analyzing the distribution of the retinal lesions in the mouse model according to claim 1, wherein a process of acquiring the retinal layering distribution based on the coordinate map of the lesion distribution rule, and calculating and counting the lesion distribution quadrants comprises:

calculating and recording the quadrants with lesion coordinates based on an IF function tool; recording as 0 when there is no lesion in the quadrants; recording as 1 when a lesion is located in a first quadrant, recording as 2 when a lesion is located in a second quadrant, recording as 3 when a lesion is located in a third quadrant, recording as 4 when a lesion is located in a fourth quadrant, and recording as 5 when a lesion is located in a coordinate axis; and classifying recorded results according to an eye type, a mouse type and a location, and generating distribution quadrant histograms by a statistical analysis with a t test.

6. The method for analyzing the distribution of the retinal lesions in the mouse model according to claim 1, wherein a process of counting the number of lesions based on the retinal layering distribution comprises:

counting the number of lesions respectively based on the t test according to the retinal layering involved in the lesions in OCT, and generating histograms of the number of the lesions.

\* \* \* \* \*